United States Patent
Wang et al.

(10) Patent No.: US 9,585,984 B2
(45) Date of Patent: Mar. 7, 2017

(54) ANTIBACTERIAL CORNEA REPAIR MATERIAL AND PREPARATION METHOD THEREOF

(71) Applicant: South China University of Technology, Guangzhou (CN)

(72) Inventors: Yingjun Wang, Guangzhou (CN); Yang Liu, Guangzhou (CN); Li Ren, Guangzhou (CN)

(73) Assignee: SOUTH CHINA UNIVERSITY OF TECHNOLOGY, Guangzhou, Guangdong Province (CN)

( * ) Notice: Subject to any disclaimer, the term of this patent is extended or adjusted under 35 U.S.C. 154(b) by 0 days.

(21) Appl. No.: 14/891,604

(22) PCT Filed: Dec. 20, 2013

(86) PCT No.: PCT/CN2013/090086
§ 371 (c)(1),
(2) Date: Nov. 16, 2015

(87) PCT Pub. No.: WO2014/183445
PCT Pub. Date: Nov. 20, 2014

(65) Prior Publication Data
US 2016/0082151 A1 Mar. 24, 2016

(30) Foreign Application Priority Data
May 16, 2013 (CN) .......................... 2013 1 0181772

(51) Int. Cl.
| | |
|---|---|
| *A61F 2/14* | (2006.01) |
| *A61L 27/24* | (2006.01) |
| *C07K 14/78* | (2006.01) |
| *A61L 27/36* | (2006.01) |
| *A61L 27/54* | (2006.01) |

(52) U.S. Cl.
CPC .............. *A61L 27/24* (2013.01); *A61F 2/142* (2013.01); *A61L 27/3687* (2013.01); *A61L 27/3691* (2013.01); *A61L 27/54* (2013.01); *C07K 14/78* (2013.01); *A61L 2300/406* (2013.01); *A61L 2430/16* (2013.01)

(58) Field of Classification Search
CPC ..... A61F 2/142; A61F 9/0017; A61K 9/0048; A61L 27/24; A61L 27/48; A61L 27/54; A61L 27/3687; A61L 27/3691; A61L 2300/406; A61L 2430/16; C07K 14/78; C08H 1/00; C08L 89/00
See application file for complete search history.

(56) References Cited

U.S. PATENT DOCUMENTS

| | | | | | |
|---|---|---|---|---|---|
| 5,259,998 | A | * | 11/1993 | Reich | ............... B29D 11/00096 264/1.1 |
| 2005/0163818 | A1 | | 7/2005 | Sung et al. | |
| 2008/0317818 | A1 | * | 12/2008 | Griffith | ................ A61K 9/0051 424/427 |

FOREIGN PATENT DOCUMENTS

| | | |
|---|---|---|
| CN | 101480505 | 7/2009 |
| CN | 102989038 | 3/2013 |
| CN | 103272268 | 9/2013 |

OTHER PUBLICATIONS

International Search Report for PCT/CN2013/090086 dated Mar. 27, 2014, and English language translation, 6 pages total.

* cited by examiner

*Primary Examiner* — Jeffrey E Russel
(74) *Attorney, Agent, or Firm* — Hamre, Schumann, Mueller & Larson, P.C.

(57) ABSTRACT

A preparation method of an antibacterial cornea repair material includes (1) purifying type I collagen extracted from beef tendons, and preparing a collagen solution; (2) casting the collagen solution into a mold to form a membrane by air drying at room temperature; (3) soaking the membrane in an antibiotic solution, stirring until the membrane is in contact with the antibiotic solution, adding a crosslinking agent and a catalyst to the antibiotic solution contacted with the membrane, and stirring the antibiotic solution contacted with the membrane with the crosslinking agent and the catalyst added therein to perform a crosslinking reaction to obtain a crosslinked membrane; and (4) washing the crosslinked membrane material with deionized water, and air drying at room temperature. The antibacterial cornea repair material has relatively good mechanical properties, optical properties, biocompatibility, and antibacterial effect, and can be used for repairing and replacing damaged cornea tissue.

8 Claims, 4 Drawing Sheets

ANTIBACTERIAL CORNEA REPAIR MATERIAL AND PREPARATION METHOD THEREOF

FIELD OF THE INVENTION

The present invention relates to a preparation method of an antibacterial cornea repair material, particularly to a preparation method of a biological material that can reduce the risk of cornea inflammation reaction while it repairs damaged cornea tissue.

The material obtained by the present invention can be used for repairing and replacing the damaged cornea tissue.

BACKGROUND OF THE INVENTION

A cornea disease is a very common ophthalmic disease, which causes about one third of the blind patients in the world. Corneal transplant is an effective means of treating corneal blindness, and an allograft-donated cornea is currently the only clinically feasible cornea repair material. However, because the amount of healthy donated corneas is far less than the demand of the corneal transplant, research and development of artificial corneas seems to be very necessary.

In addition to the lack of the corneal transplant materials, how to avoid the inflammation reaction after the corneal transplant surgery is another problem faced by the corneal transplant. The current common method is postoperative frequent medication, which not only wastes a lot of drugs, but is difficult to ensure the amount of drugs and dosing time as well, also very troublesome for the patients themselves. Therefore, many tissue engineering repair materials will be loaded with drugs through physical effects such as drug package or adsorption; however, such repair materials, for the unique requirements of the cornea for optical transparency and toughness, are often very difficult to ensure their good optical and mechanical properties in addition to the drug release effect. Therefore, the cornea repair material should have an antibacterial effect in a period of postoperative wound recovery on the basis of ensuring the physicochemical and biological properties needed by the cornea repair material, which will greatly reduce the risk of inflammation reaction after the corneal transplant surgery.

CONTENTS OF THE INVENTION

The purpose of the present invention is to overcome the defects of the prior art, and provide a preparation method of a new antibacterial cornea repair material. The present invention obtains a cornea repair material having good mechanical properties, optical properties and biocompatibility by taking high-purity type I collagen and the antibiotic small molecules commonly used after the ophthalmic surgery as the raw materials at a certain ratio and by going through processes such as forming a membrane with a mould, soaking in an antibiotic solution, stirring and crosslinking, washing and air drying. Besides, the antibacterial cornea repair material provided by the present invention can also have a good antibacterial effect on such bacteria as *Staphylococcus aureus* that cause inflammation reaction after the ophthalmic surgery in a certain period. This material can be used for repairing and replacing damaged cornea tissue in the field of medicine, and can also reduce the risk of bacterial infection after the transplant surgery.

The purpose of the present invention is achieved through the following technical solution:

A preparation method of an antibacterial cornea repair material is provided, including the following steps:

(1) Purifying type I collagen extracted from beef tendons, and using an acetic acid or hydrochloric acid solution to prepare a collagen solution with a concentration of 6.0-10.0 mg/mL;

(2) casting the collagen solution into the forming mould of the cornea repair material, and then naturally air drying at room temperature to form a membrane;

(3) soaking the collagen membrane obtained in step (2) in an antibiotic solution with a concentration of 5.0-25.0 mg/mL, and stirring until the membrane is fully in contact with the solution; and then adding a crosslinking agent and a catalyst to the above-mentioned solution, and stirring to perform a crosslinking reaction; the mass ratio of the crosslinking agent to the catalyst is 4:1, and the mass ratio of the total of the collagen and antibiotics to the crosslinking agent is (5-7):1; and (4) taking out the crosslinked membrane material obtained in step (3) and washing 3-5 times with deionized water, and then naturally air drying at room temperature to obtain the antibacterial cornea repair material.

Preferably, the forming mould of the cornea repair material in step (2) has a similar geometrical shape to the cornea tissue.

Preferably, the concentration of the antibiotics in step (3) is 10.0-15.0 mg/mL.

Preferably, the antibiotics in step (3) are tobramycin, gentamicin, ofloxacin or ciprofloxacin.

Preferably, the crosslinking agent in step (3) is 1-ethyl-3 (3-dimethylaminopropyl)carbodiimide (EDC), and the catalyst is N-hydroxysuccinimide (NHS).

Preferably, the mass ratio of the total of the collagen and antibiotics to the crosslinking agent is 6:1.

Preferably, the crosslinking reaction time in step (3) is 2-6 hours.

Compared with the prior art, the present invention has the following advantages:

(1) The cornea repair material prepared by the present invention can be antibacterial in a period of postoperative wound recovery, thereby greatly reducing the risk of inflammation reaction after the corneal transplant surgery.

(2) The cornea repair material prepared by the present invention after adding antibiotics still has the similar optical properties, mechanical properties and biological properties to the natural cornea tissue.

(3) The cornea repair material prepared by the present invention can greatly facilitate the patients' postoperative care, and reduce the cost of a great number of drugs.

(4) The present invention uses a simple forming process and reduces raw material costs, conducive to mass production.

DETAILED DESCRIPTION OF THE EMBODIMENTS

Figure 1:
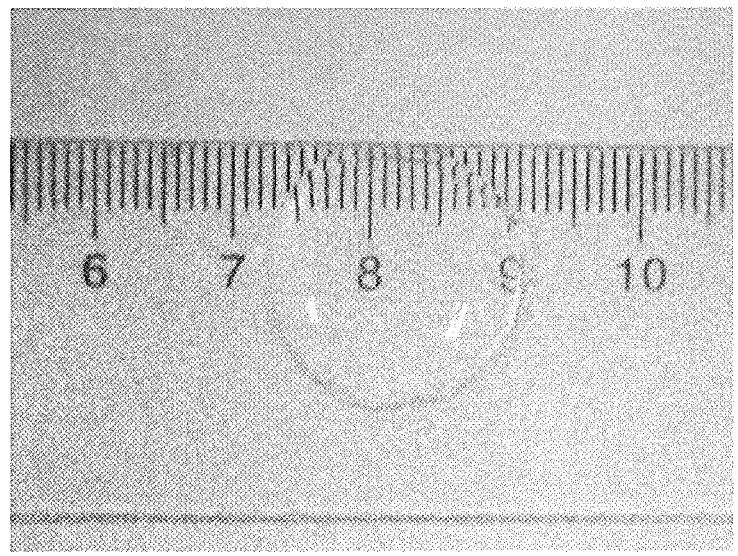
FIG. 1 shows a sample of the Tob-Col membrane of Example 1.

For a better understanding of the present invention, the present invention is further explained below in conjunction with examples, but the scope of protection claimed by the present invention is not limited thereto.

Example 1

Preparing a tobramycin-collagen crosslinked membrane (Tob-Col) material by taking tobramycin and collagen (Col) as raw materials. This Tob-Col membrane material is prepared by the following steps:

(1) Purifying type I collagen extracted from beef tendons, and using hydrochloric acid to prepare a collagen solution with a concentration of 6 mg/mL;

(2) casting 8 mL collagen solution with a concentration of 6 mg/mL into the forming mould of the cornea repair material, and then naturally air drying at room temperature to form a membrane;

(3) soaking the collagen membrane obtained in step (2) in a tobramycin solution with a concentration of 15 mg/mL, and stirring until the collagen membrane is fully in contact with the tobramycin solution; and (4) adding EDC and NHS (EDC:NHS=4:1) to the solution of step (3), with the mass ratio of the total of the collagen and tobramycin to EDC at 6:1, and stirring to perform a crosslinking reaction; taking out the crosslinked membrane material obtained after 2 hours, and washing 3 times with deionized water, and then naturally air drying at room temperature to form the Tob-Col membrane.

Example 2

Preparing a gentamicin-collagen crosslinked membrane (Gen-Col) material by taking gentamicin and collagen (Col) as raw materials. This Gen-Col membrane material is prepared by the following steps:

(1) Purifying type I collagen extracted from beef tendons, and using hydrochloric acid to prepare a collagen solution with a concentration of 8 mg/mL;

(2) casting 8 mL collagen solution with a concentration of 8 mg/mL into the forming mould of the cornea repair material, and then naturally air drying at room temperature to form a membrane;

(3) soaking the collagen membrane obtained in step (2) in a gentamicin solution with a concentration of 15 mg/mL, and stirring until the collagen membrane is fully in contact with the gentamicin solution;

(4) adding EDC and NHS (EDC:NHS=4:1) to the solution of step (3), with the mass ratio of the total of the collagen and gentamicin to EDC at 6:1, and stirring for 3 hours so that the antibiotic small molecules can undergo a crosslinking reaction with the collagen; and (5) taking out the crosslinked membrane material obtained in step (4) and washing 3 times with deionized water, and then naturally air drying at room temperature to form the Gen-Col membrane.

Example 3

Preparing a ciprofloxacin-collagen crosslinked membrane (Cip-Col) material by taking ciprofloxacin and collagen (Col) as raw materials. This Cip-Col membrane material is prepared by the following steps:

(1) Purifying type I collagen extracted from beef tendons, and using acetic acid to prepare a collagen solution with a concentration of 8 mg/mL;

(2) casting 8 mL collagen solution with a concentration of 8 mg/mL into the forming mould of the cornea repair material, and then naturally air drying at room temperature to form a membrane;

(3) soaking the collagen membrane obtained in step (2) in a ciprofloxacin solution with a concentration of 5 mg/mL, and stirring until the collagen membrane is fully in contact with the ciprofloxacin solution;

(4) adding EDC and NHS (EDC:NHS=4:1) to the solution of step (3), with the mass ratio of the total of the collagen and ciprofloxacin to EDC at 6:1, and stirring for 4 hours so that the ciprofloxacin molecules can undergo a crosslinking reaction with the collagen; and (5) taking out the crosslinked membrane material obtained in step (4) and washing 3 times with deionized water, and then naturally air drying at room temperature to form the Cip-Col membrane.

Example 4

Preparing an ofloxacin-collagen crosslinked membrane (Ofl-Col) material by taking ofloxacin and collagen (Col) as raw materials. This Ofl-Col membrane material is prepared by the following steps:

(1) Purifying type I collagen extracted from beef tendons, and using hydrochloric acid to prepare a collagen solution with a concentration of 10 mg/mL;

(2) casting 8 mL collagen solution with a concentration of 10 mg/mL into the forming mould of the cornea repair material, and then naturally air drying at room temperature to form a membrane;

(3) soaking the collagen membrane obtained in step (2) in an ofloxacin solution with a concentration of 25 mg/mL, and stirring until the collagen membrane is fully in contact with the ofloxacin solution;

(4) adding EDC and NHS (EDC:NHS=4:1) to the solution of step (3), with the mass ratio of the total of the collagen and ofloxacin to EDC at 6:1, and stirring for 6 hours so that the antibiotic small molecules can undergo a crosslinking reaction with the collagen; and (5) taking out the crosslinked membrane material obtained in step (4) and washing 3 times with deionized water, and then naturally air drying at room temperature to form the Ofl-Col membrane.

Figure 2:
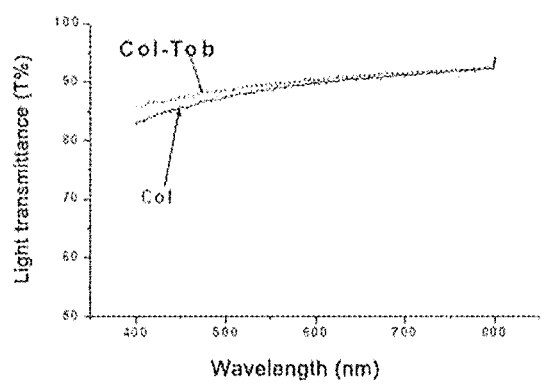
FIG. 2 shows light transmittance of the Tob-Col membrane of Example 1 and the Col membrane of the control group.
Figure 3:
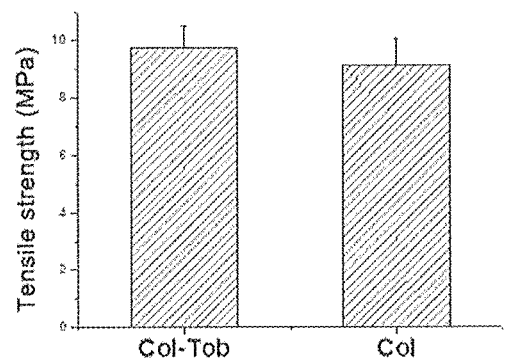
FIG. 3 shows tensile strength of the Tob-Col membrane of Example 1 and the Col membrane of the control group.
Figure 4:
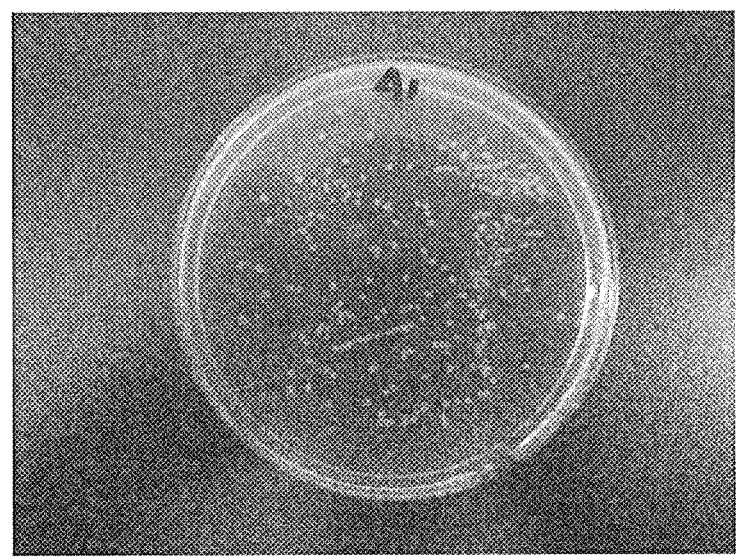
FIG. 4 shows growth of the *Staphylococcus aureus* on the Col membrane.
Figure 5:
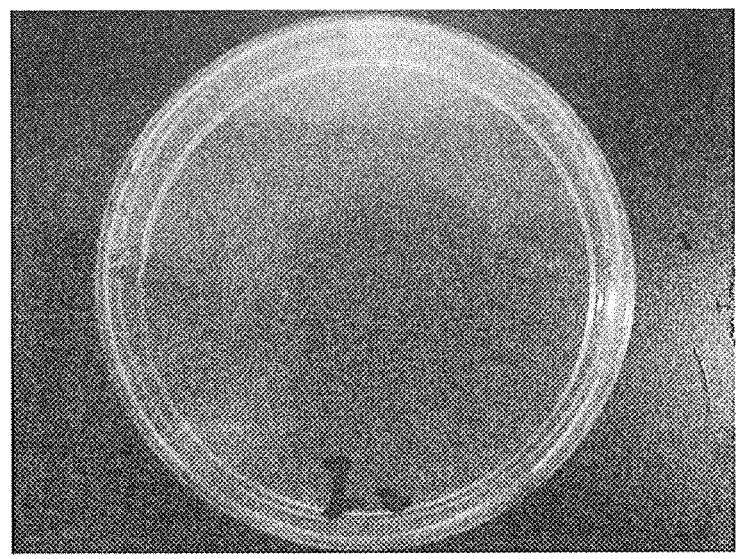
FIG. 5 shows growth of the *Staphylococcus aureus* on the Tob-Col membrane of Example 1.
Figure 6:
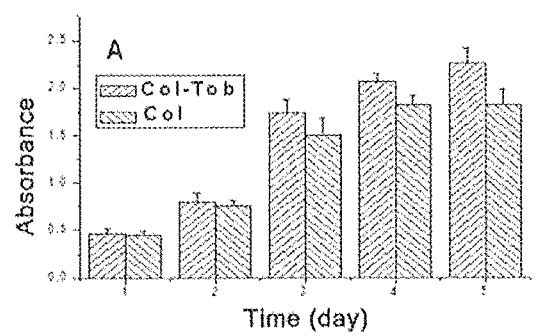
FIG. 6 shows cytotoxicity test results of the Tob-Col membrane of Example 1 and the Col membrane of the control group.
Figure 7:
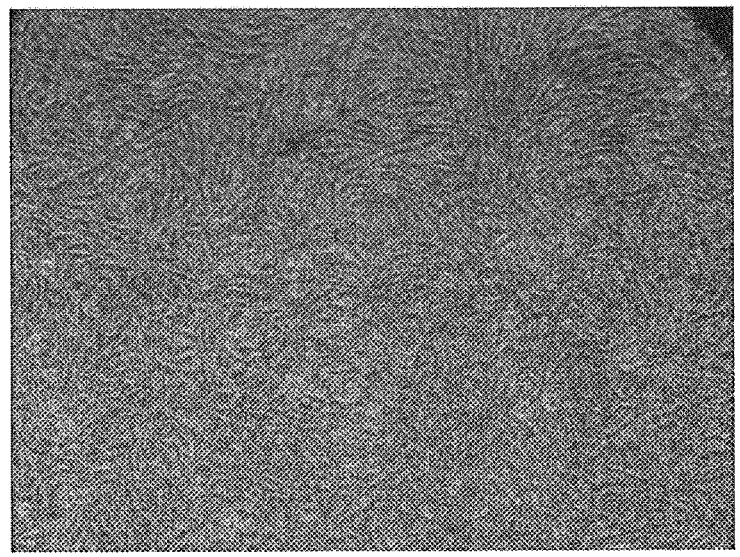
FIG. 7 shows growth of the human corneal epithelial cells on the Tob-Col membrane material of Example 1.
Figure 8:
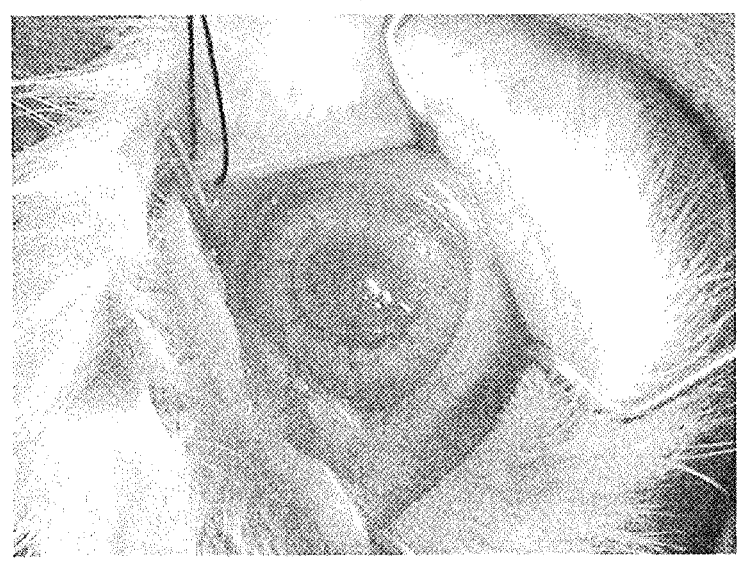
FIG. 8 shows the corneal transplant of the Tob-Col membrane of Example 1 on the animal ocular surface.

By characterization of the physicochemical properties of the materials in Example 1, FIGS. 1 and 2 show that the Tob-Col cornea repair material has good optical properties, and FIG. 3 indicates that the Tob-Col membrane has suitable mechanical properties; FIGS. 4 and 5 indicate that the Tob-Col membrane has good antibacterial properties with respect to the Col membrane; FIGS. 6 and 7 show proliferation of the human corneal epithelial cells on the Tob-Col membrane as well as the cell morphology, respectively, indicating that the cells can stably proliferate on the material and can be tightly attached to the surface of the material, with the normal spindle appearance of the cells maintained. FIG. 8 is a postoperative photograph of a New Zealand white rabbit after the lamellar corneal transplant of the Tob-Col membrane after the cornea is cut off and stripped with a trephine and a blade, wherein it can be seen that this material can withstand suturing with the ophthalmic surgical suture and can remain transparent on the ocular surface.

What is claimed is:

1. A preparation method of an antibacterial cornea repair material, comprising:
    (1) purifying type I collagen extracted from beef tendons, and using an acetic acid or hydrochloric acid solution to prepare a collagen solution with a concentration of 6.0-10.0 mg/mL;
    (2) casting the collagen solution into a mould of an antibacterial cornea repair material, and air drying the collagen solution at room temperature to form a collagen membrane;
    (3) soaking the collagen membrane obtained in step (2) in an antibiotic solution containing 5.0-25.0 mg/mL of an antibiotic, stirring the antibiotic solution until the collagen membrane is in contact with the antibiotic solution, adding a crosslinking agent and a catalyst to the antibiotic solution contacted with the collagen membrane, stirring to perform a crosslinking reaction to obtain a crosslinked membrane material, wherein the crosslinking agent to the catalyst is in a mass ratio of 4:1, and a total of the collagen membrane and the antibiotic to the crosslinking agent is in a mass ratio of (5-7):1; and
    (4) taking out the crosslinked membrane material obtained in step (3), washing the crosslinked membrane material 3-5 times with deionized water, and air drying the crosslinked membrane material at room temperature to obtain the antibacterial cornea repair material.

2. The preparation method according to claim 1, wherein the mould of the antibacterial cornea repair material in step (2) has a geometrical shape similar to a cornea tissue.

3. The preparation method according to claim 1, wherein the antibiotic solution in step (3) contains 10.0-15.0 mg/mL of an antibiotic.

4. The preparation method according to claim 1, wherein the antibiotic in step (3) includes at least one of tobramycin, gentamicin, ofloxacin and ciprofloxacin.

5. The preparation method according to claim 1, wherein the crosslinking agent in step (3) is 1-ethyl-3(3-dimethylaminopropyl)carbodiimide, and the catalyst is N-hydroxysuccinimide.

6. The preparation method according to claim 1, wherein the mass ratio of the total of the collagen and antibiotic to the crosslinking agent is 6:1.

7. The preparation method according to claim 1, wherein the crosslinking reaction in step (3) is conducted for 2-6 hours.

8. An antibacterial cornea repair material prepared by the method according to claim 1.

* * * * *